United States Patent [19]

Panster et al.

[11] Patent Number: 4,855,470

[45] Date of Patent: Aug. 8, 1989

[54] ORGANOSILANES CONTAINING BENZOYL THIOUREA GROUPS AND METHOD OF PREPARATION

[75] Inventors: Peter Panster, Rodenbach; Horst Grethe; Peter Kleinschmit, both of Hanau, all of Fed. Rep. of Germany

[73] Assignee: Degussa Aktiengesellschaft, Frankfurt, Fed. Rep. of Germany

[21] Appl. No.: 154,408

[22] Filed: Feb. 10, 1988

[30] Foreign Application Priority Data

Feb. 28, 1987 [DE] Fed. Rep. of Germany ....... 3706521

[51] Int. Cl.[4] .............................................. C07F 7/10
[52] U.S. Cl. ................................................... 556/421
[58] Field of Search ........................................ 556/421

[56] References Cited

U.S. PATENT DOCUMENTS 3,208,971  9/1965  Gilkey et al. .................... 556/421 X
3,642,855  2/1972  Berger .......................... 556/421 UX
4,234,573  11/1980  Böger et al. ..................... 556/421 X

FOREIGN PATENT DOCUMENTS 0379580  7/1973  U.S.S.R. ............................ 556/421

Primary Examiner—Paul F. Shaver
Attorney, Agent, or Firm—Beveridge, DeGrandi & Weilacher

[57] ABSTRACT

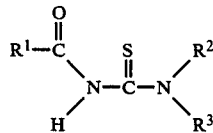

are presented in which $R^1$=phenyl or nitrophenyl, $R^2$ is an entity of the formula

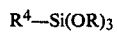

$R^4$=alkylene, cycloalkylene or an entity of the formula:

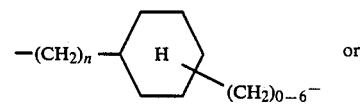

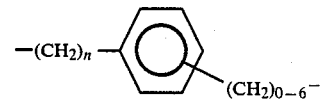

whereby $n=1-6$, R=alkyl containing $C_1$-$C_3$ and $R^3=R^2$ or H. A method of preparing these compounds is also disclosed.

9 Claims, No Drawings

ORGANOSILANES CONTAINING BENZOYL THIOUREA GROUPS AND METHOD OF PREPARATION

The present invention relates to new organosilanes containing benzolythiourea groups which can be used to prepare insoluble metal adsorbent systems based on inorganic polymer backbones. In addition, the present invention pertains to methods of preparing these new products.

The separation of metals from aqueous and orgainic solutions represents a large problem in various branches of industry. Various methods and techniques are practiced today; e.g. in order to recover valuable metals or in order to protect the environment. It is frequently customary to use suitable modified organic polymers (e.g. DD-PS Nos. 207,915; 212,190; 212,257 or U.S. Pat. No. 4,448,694) or to employ liquid or dissolved complexing agents (DE-PS Nos. 33 40 055 and 33 40 056; DE-OS No. 33 47 406).

However, these methods are frequently not practical. On the one hand, the organic polymer carriers used are not equal to the requirements due to their low temperature stability and solvent stability and on the other hand, the use of liquid or dissolved complexing agents requires an industrial expense which can be considerable.

It is asically more advantageous to use systems which are based on an inorganic polymer backbone, as is the case, for example, with silica gel. Such system exhibit a greater temperature stability and solvent stability (GB No. 1,532,295).

SUMMARY OF THE INVENTION

It is an object of the present invention to provide suitably substituted organosilanes which can be used to prepare metal adsorbent systems based on an inorganic polymer backbone. In accomplishing this object, conventional inorganic polymer systems such as e.g. $SiO_2$, $Al_2O_3$, $TiO_2$ are used and modified. Alternatively, corresponding organofunctional polysiloxanes are prepared. In attaining this and other objects, one feature of the invention resides in using a benzoyl thiourea group as a complexing entity which has proven to be especially effective (DE-PS Nos. 33,40 055 and 33 40 056 or DD-PS No. 212,190).

According to the primary feature of the present invention, there are provided new organosilanes containing benzoyl thiourea groups represented by the formula:

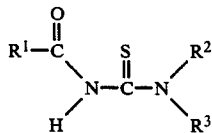

whereby $R^1$ is phenyl or a phenyl group substituted with an $NO_2$ group, $R^2$ is represented by the formula

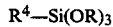

in which $R^4$ is an alkylene group with from 1 to 10 C atoms or a cycloalkylene group from 5 to 8 C atoms, or is a group represented by the formulas:

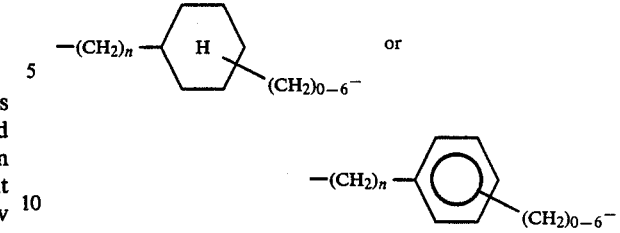

in which n can be a number from 1 to 6, and R is a linear or branched alkyl group with 1 to 3 C atoms, $R^3$ has the same meaning as $R^2$ and can be identical with or different from $R^2$, or $R^3$ is H.

In the compounds of the invention according to formulas (1) and (2), $R^4$ can be a linear or branched alkylene group.

In a preferred aspect of the invention, there are provided organosilanes containing benzoyl thiourea groups according to the formula:

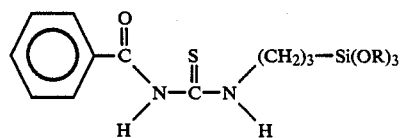

in which R is methyl or ethyl. This preference results especially from the particularly good availability of the initial materials.

According to another preferred aspect of the invention, there are provided organosilanes containing benzoyl thiourea groups according to the formula:

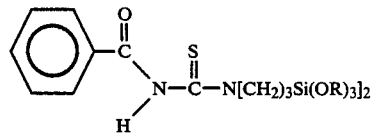

This group of compounds are also distinguished by an especially good availability of the intial materials and by the particularly good properties of the organopolysiloxanes which can be prepared from them.

A skillfull further aspect of the present invention relates to a method for preparing the new compounds, as described above. In essential details this method involves the reaction of an organosilane amine of the formula:

in which $R^2$ and $R^3$ have the same meaning as above, with an isothiocyanate of the formula

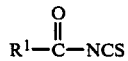

in which $R^1$ has the same meaning as above. The temperature of the reaction is not critical and thus can be below, at or above room temperature, up to a temperature of 100° C. Preferably, the temperature is −30° C. to +50° C. Pressure can vary from normal pressure to a superpressure which corresponds to the sum of the partial pressures at the particular temperature of reaction.

The reaction can be described by the following equation:

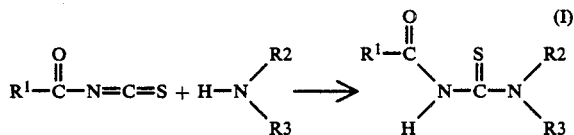

Examples of especially important primary and secondary organosilane amines which are used especially in the preparation or compounds according to the preferred aspects of the invention are:

and

and their corresponding methoxy homologs. These intitial starting materials are available on a commercial basis. the reaction of an isothiocyanate with a primary or secondary amine is a reaction known in principle in organic synthesis and is also described in a prior patent; e.g. EP-OS No. 0,126,934. The synthesis of acyl isothiocyanates is likewise know in principle, which can be prepared from the corresponding benzoyl chlorides and alkali—or ammonium rhodanide in an inert and largely water-free organic solvent according to the equation

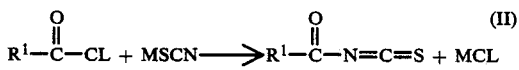

Suitable organic solvents are e.g. acetone, methyl ethyl ketone, tetrahydrofurane or dixane. The reaction takes place as a rule even at room emperature and at a relatively high speed and can be accelerated even more by the addition of a phase transfer catalyst.

The exothermal reaction according to equation (I) also occurs very spontaneously even at low temperatures according to the method of the invention as set forth above. Therefore, in order to avoid possible secondary reactions, relatively low temperatures are basically preferred; a particularly advantageous range is at temperatures from −30° C. to +50° C. Although other stoichiometric ratios can also be used in principle, a 1:1 molar stoichiometry according to equation (I) is to be preferred.

It is also generally possible to prepare the organosilanes containing benzoyl thiourea groups in accordance with the invention by means of a reaction according to equation (III)

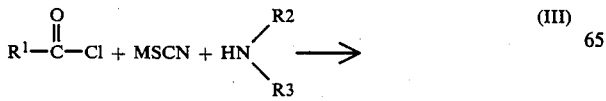

-continued

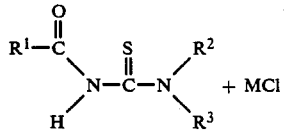

according to which only an "in situ" formation of the benzoyl isothiocyanate component occurs. However, this reaction is disadvantageous compared to the method of the invention as shown in equation I above on account of increased by-product formation.

According to the method of preparation in accordance with the invention, the use of a solvent can basically be dispensed with.

However, the ue of a largely water-free solvent can prove to be advantageous as regards greater product purity and a better practicable perfomance. Suitable solvents for this are, among others, toluene, xylene, chlorinated hydrocarbons, open-chain and cyclic ethers or ester such as e.g. acetoacetic ester, aliphatic or cycloaliphatic hydrocarbons with 5 to 8 C atoms. Especially preferred are linear or branced alcohols with 1 to 3 C atoms and acetone or methylethyl ketone.

The organosilanes containing benzoyl thiourea groups according to the invention are monomers and are bright-yellow to orange-colored liquids which all boil far above 200° C. Since the new products can be obtained in accordance with the method of the invention in a degree of purity suffiecient for all practicable applications, a further purification by distillation, which is associated in almost all instances with an at least partial decomposition, can be eliminated.

DETAILED DESCRIPTION OF THE INVENTION

The invention is illustrated in further detail in the following examples.

EXAMPLE 1

200 g (0.903 mole) $H_2N-(CH_2)_3-Si(OC_2H_5)_3$ (aminopropyl triethoxysilane) were put in a 1 l four-neck flask rinsed with dry nitrogen and fitted with KPG agitator, drop funnel, reflux condenser and inner thermometer. Within one hour, 147,4 g (0.903 mole) benzoyl isothiocyanate were dosed into the aminosilane in the flask.

The inner temperature was maintained at 20° C. by cooling with a water bath. After a further 1-hour agitation at room temperature, the orange-colored liquid was freed from highly volatile constituents in a thin-film evaporator at a temperatur of 120° C./1 mbar. There was obtained 334.8 g product (96.4% of theory) whose analytical data and NMR spectrum were in agreement with the chemical structure

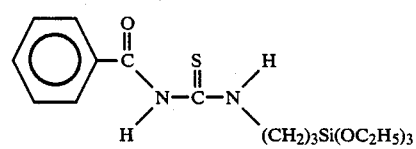

which remained in the bottom of the thin-film evaporator.

|          | % C   | % H  | % N  | % S  | % Si |
|----------|-------|------|------|------|------|
| Theory:  | 53.10 | 7.34 | 7.28 | 8.34 | 7.30 |
| Found:   | 52.83 | 7.42 | 7.37 | 8.21 | 7.12 |

$^1$H—NMR spectrum (CDCl$_3$/250 MHz): δ—CH$_2$Si—0.72 ppm, δ—CH$_2$—1.85 ppm, δN—CH$_2$—3.75 ppm, δortho C—H—7.85 ppm, δmeta C—H—7.5 ppm, δpara C—H—7.6 ppm.

EXAMPLE 2

200 g (1.12 mole) H$_2$N—(CH$_2$)$_3$—Si(OCH$_3$)$_3$ (aminopropyl trimethoxysilane) and 182.0 g (1.12 mole) benzoyl isothiocyanate were reacted analogously as in example 1 and the raw product obtained was worked up and treated in the same manner.

There was obtained 368.4 g (96.0% of theory) of the benzoyl thiourea-functional silane of the formula

[structure: phenyl-C(=O)-N(H)-C(=S)-N(H)-(CH$_2$)$_3$-Si(OCH$_3$)$_3$]

|          | % C   | % H  | % N  | % S  | % Si |
|----------|-------|------|------|------|------|
| Theory:  | 49.10 | 6.48 | 8.18 | 9.36 | 8.20 |
| Found:   | 49.10 | 6.52 | 8.08 | 9.27 | 8.04 |

$^1$H—MNR spectrum (CDCl$_3$/250 MHz): analogously to example 1.

EXAMPLE 3

150 g (0.54 mole) H$_2$N—(CH$_2$)$_{10}$—Si(OCH$_3$)$_3$ (aminodecyl trimethoxysilane) and 88.2 g (0.54 mole) benzoyl isothiocyanate were reacted in an analogous manner with example 1 in 200 ml dried acetone at 40° C. After the acetone was removed in a rotary evaporator at 50° C./100 mbar and the raw product was purified in a thin-layer evaporator, 224.1 g (94.1% of theory) of the benzoyl thiourea-functional silane of the formula

[structure: phenyl-C(=O)-N(H)-C(=S)-N(H)-(CH$_2$)$_{10}$-Si(OCH$_3$)$_3$]

were obtained.

|          | % C   | % H  | % N  | % S  | % Si |
|----------|-------|------|------|------|------|
| Theory:  | 57.24 | 8.23 | 6.36 | 7.28 | 6.37 |
| Found:   | 57.36 | 8.36 | 6.19 | 7.09 | 6.12 |

EXAMPLE 4

100 g (0.42 mole)

H$_2$N—CH$_2$CH(CH$_3$)CH$_2$—Si(OC$_2$H$_5$)$_3$ and 88.4 g (0.42 mole) of the compound formula:

[structure: O$_2$N-phenyl-C(=O)-NCS]

were reacted in an analogous manner with example 3 in 100 ml dried ethanol at 20° C. After a work-up as in example 3, 170.2 g product (90.3% of theory) of the formula

[structure: O$_2$N-phenyl-C(=O)-N(H)-C(=S)-N(H)-CH$_2$CH(CH$_3$)CH$_2$-Si(OC$_2$H$_5$)$_3$]

were obtained.

|          | % C   | % H  | % N  | % S  | % Si |
|----------|-------|------|------|------|------|
| Theory:  | 48.74 | 6.59 | 9.47 | 7.23 | 6.33 |
| Found:   | 48.52 | 6.70 | 9.22 | 7.04 | 6.11 |

EXAMPLE 5

200 g (0.47 mole) HN[(CH$_2$)$_3$Si(OC$_2$H$_5$)$_3$]$_2$ and 76.7 g (0.47 mole) benzoyl isothiocyanate were reacted in an analogous manner with example 1 in 200 ml dried ethanol under ice cooling at 10° C. After a 1-hour subsequent reaction at room temperature, the distillative removal of the ethanol in a rotary evaporator at 50° C./100 mbar and purification of the raw product in a thin-layer evaporator, 262.0 g (94.7% of theory) of the benzoyl thiourea-functional silane of the formula

[structure: phenyl-C(=O)-N(H)-C(=S)-N[(CH$_2$)$_3$Si(OC$_2$H$_5$)$_3$]$_2$]

were obtained.

|          | % C   | % H  | % N  | % S  | % Si |
|----------|-------|------|------|------|------|
| Theory:  | 53.03 | 8.22 | 4.76 | 5.44 | 9.54 |
| Found:   | 52.79 | 8.12 | 4.67 | 5.30 | 9.39 |

EXAMPLE 6

126.2 g (91.0% of theory) of the product

[structure: 2-NO$_2$-phenyl-C(=O)-N(H)-C(=S)-N[(CH$_2$)$_{10}$Si(OCH$_3$)$_3$]$_2$]

were obtained form 100 g (0.19 mole) HN[(CH$_2$)$_{10}$Si(OCH$_3$)$_3$]$_2$ and 38.7 g (0.19 mole)

[Structure: 2-nitrobenzoyl isothiocyanate]

analogously with example 5 after reaction in 100 ml methanol at 20° C.

|  | % C | % H | % N | % S | % Si |
|---|---|---|---|---|---|
| Theory: | 54.73 | 8.51 | 5.63 | 4.30 | 7.53 |
| Found: | 54.49 | 8.31 | 5.67 | 4.25 | 7.35 |

EXAMPLE 7

142.3 g (91.9% of theory) of the product

[Structure: benzoyl thiourea with CH2-phenyl-CH2CH2Si(OC2H5)3 substituent]

where obtained from 100 g (0.34 mole)

[Structure: H2N—CH2—phenyl—CH2CH2—]

Si(OC2H5)3 and 54.9 g (0.34 mole) benzoyl isothiocyanate analogously with example 5 after reaction in 100 ml dried ethanol at 20° C.

| Theory: | 59.97 | 7.00 | 6.08 | 6.96 | 6.10 |
|---|---|---|---|---|---|
| Found: | 59.58 | 7.24 | 5.86 | 6.72 | 5.91 |

Further variations and modifications of the foregoing will be apparent to those skilled in the art from a reading thereof and are intended to be encompassed by the claims appended hereto.

German priority applicaion No. P 37 06 521.1-42 is relied on and incorporated by reference.

We claim:

1. An organosilane containing benzol thiourea compound of the formula

[Structure (formula with $R^1$, $R^2$, $R^3$)]

whereby
   $R^1$ stands for phenyl or for a phenyl group substituted with an $NO_2$ group,
   $R_2$ is of the formula $R^4$—Si(OR)$_3$ in which
   $R^4$ is alkylene with 1 to 10 C atoms or cycloalkylene with 5 to 8 C atoms, or of the formula

[Structure (formula 5)]

in which n is a number from 1 to 6,
and R is linear or branched alkyl with 1 to 3 C atoms,
   $R^3$ has the same meaning as $R^2$ and can be identical with or different from $R^2$ or $R^3$ is H.

2. An organosilane containing benzoyl thiourea compound according to claim 1, wherein R4 is a linear or branched alkylene.

3. An organosilane containing benzoyl thiourea compound according to claim 1 with the formula

[Structure (3)]

in which R is for methyl or ethyl.

4. An organosilane containing benzoyl thiourea compound according to claim 1 with the formula

[Structure (4): ...N—C(=S)—N[(CH2)3Si(OR)3]2]

in which R is for methyl or ethyl.

5. A method of preparing a compound according to claim 1 comprising reacting an organosilane amine of the formula

[Structure (5): H—N(R2)(R3)]

in which $R^2$ and $R^3$ have the same meaning as in claim 1, with an isothiocyanate of the formula $R^1$—C(=O)—NCS    (6)

in which $R^1$ has the same meaning as in claim 1.

6. The method according to claim 5 wherein the reaction takes place below, at or above room temperature up to a temperature of 100° C. until the complete reaction of the isothiocyanate function in formula (6).

7. The method according to claim 5 wherein the reaction takes place at normal pressure or a superpressure which corresponds to the sum of the partial pressures at the particular temperature.

8. The method according to claim 6, wherein the temperature is −30° C. to +50° C.

9. The method according to claim 6 wherein a linear or branched alcohol with 1 to 3 C atomes, acetone or methylethyl ketone is used as solvent in the reaction of the amine of formula (5) with the isothiocyanate of formula (6).

* * * * *